United States Patent
Carlson et al.

(10) Patent No.: US 11,078,137 B1
(45) Date of Patent: Aug. 3, 2021

(54) SUSTAINABLE TERPENE EXTRACTION METHOD

(71) Applicants: Stephen Carlson, Folsom, CA (US);
James Stegall, Granite Bay, CA (US);
Michael Cook, Las Vegas, NV (US);
Donny Jones, Snohomish, WA (US)

(72) Inventors: Stephen Carlson, Folsom, CA (US);
James Stegall, Granite Bay, CA (US);
Michael Cook, Las Vegas, NV (US);
Donny Jones, Snohomish, WA (US)

(73) Assignee: Buddies IP Holding, Inc., Henderson, NV (US)

( * ) Notice: Subject to any disclaimer, the term of this patent is extended or adjusted under 35 U.S.C. 154(b) by 0 days.

(21) Appl. No.: 16/813,096

(22) Filed: Mar. 9, 2020

Related U.S. Application Data

(60) Provisional application No. 62/815,537, filed on Mar. 8, 2019.

(51) Int. Cl.
*C07C 7/09* (2006.01)

(52) U.S. Cl.
CPC ........................ *C07C 7/09* (2013.01)

(58) Field of Classification Search
CPC ................ C07C 7/09; C07C 7/04; C07C 7/00
See application file for complete search history.

(56) References Cited

U.S. PATENT DOCUMENTS

| 5,061,502 | A | * | 10/1991 | Cully | ...................... C11B 9/022 426/422 |
| 9,592,457 | B2 | * | 3/2017 | Dabao | ................ B01D 11/0296 |
| 9,649,349 | B1 | | 5/2017 | Tucker | |
| 2016/0346339 | A1 | * | 12/2016 | Finley | ................... A61K 31/355 |
| 2017/0020944 | A1 | * | 1/2017 | Towle | .................... B01D 3/143 |
| 2017/0333503 | A1 | * | 11/2017 | Ayres | .................... A61K 36/185 |

FOREIGN PATENT DOCUMENTS

| WO | WO-2016064987 A1 * | 4/2016 | .............. A61P 25/18 |
| WO | WO 2016/200438 | 12/2016 | |

\* cited by examiner

*Primary Examiner* — Youngsul Jeong
(74) *Attorney, Agent, or Firm* — Heisler & Associates

(57) ABSTRACT

The method begins with an oil which in one embodiment is cannabis crude oil derived from a cannabis plant. Oil is placed within a container having an open upper portion and with the oil preferably only filling up less than half of a volume of the container. The container and oil therein are placed within a vacuum oven where the oil is heated over time to a preselected temperature. A vacuum is then drawn on the oil while it is within the oven. Initial vacuum application is carefully applied to avoid the oil boiling over and out of the container. Vacuum residence time continues for a preselected duration, while gaseous terpenes are drawn from the oven toward the source of vacuum, such as a vacuum pump, by way of a cold trap/condenser. This cold trap is sufficiently cold that terpenes are condensed into a liquid form and collected therein.

20 Claims, 2 Drawing Sheets

SUSTAINABLE TERPENE EXTRACTION METHOD

CROSS-REFERENCE TO RELATED APPLICATIONS

This application claims benefit under Title 35, United States Code § 119(e) of U.S. Provisional Application No. 62/815,537 filed on Mar. 8, 2019.

FIELD OF THE INVENTION

The following invention relates to methods and systems for extracting terpenes from various different plants or other cellulosic materials. More particularly, this invention relates to terpene extraction methods which extract terpenes from oils produced from plant materials including portions of the cannabis plant.

BACKGROUND OF THE INVENTION

As with any solid biological material, a large number of separate chemical constituents are contained therein. These chemical constituents are largely in the form of organic molecules which have various different characteristics. The various species of the cannabis plant similarly exhibit such a multiplicity of separate chemical constituents. One particular hydrocarbon chemical constituent category present within many plants, including various species of cannabis, are generally identified as terpenes. Terpenes are a large and diverse class of compounds which often have a strong odor. Although sometimes used interchangeably with "terpenes," terpenoids (or isoprenoids) are modified terpenes as they contain additional functional groups, usually oxygen-containing and are generally of artificial origin rather than being merely extracted in their natural form. Whether for their odor associated properties, or for other beneficial characteristics, it is desirable to extract terpenes from the cannabis plant, so that such terpenes can be beneficially used.

Prior art terpene extraction techniques are characterized by multiple drawbacks. The drawbacks include low yield, long processes, high expense processes and excessive presence of impurities within the extracted terpenes. Accordingly, a need exists for improved methods of terpene extraction, particularly adapted for use in extracting terpenes from various species of the cannabis plant. Terpenoids of artificial manufacture or other suspect providence are in common use, but are generally inferior, resulting in deception and/or confusion in the marketplace when not properly identified as artificial in nature, and produced by less sustainable manufacturing processes.

SUMMARY OF THE INVENTION

With this invention, a method for terpene extraction from various species of the cannabis plant is provided. This method is environmentally sustainable, requiring small amounts of energy input and produces an exceptionally high yield and highly purified terpene extract. Initially, cannabis crude oil is provided for input into the method and process of this invention. This cannabis crude oil is liquid in form and can result from various different methods of primary extraction. These methods of primary extraction are well understood by those skilled in the art and so are not further disclosed here, but generally can include one or more of extraction by heat and/or pressure, ethanol extraction, hydrocarbon extraction, steam extraction, $CO^2$ extraction, etc.

The cannabis crude oil is processed according to one form of this extraction method utilizing a vacuum oven with a cold trap and utilizing a separatory funnel. An example of such a vacuum oven is a vacuum oven with window such as those provided by CascadeTek of Cornelius, Oreg. An example of a suitable cold trap would be a Labconco Cold Trap, available from Grainger, Inc. of Lake Forest, Ill. These processing elements of equipment are known in the prior art, and variations thereof can be acceptably used according to the method of this invention. In general, the vacuum oven includes a pressure tight enclosure with a heat source that is able to heat an interior of the oven, which can be any of a variety of different heat sources, including conduction heat sources, convection heat sources, microwave energy or other radiative heat energy sources, or various combinations thereof. The oven would also typically include a vacuum pump for removal of air/gas from within the oven, which can be both turned on and off, as well as being throttleable to control a rate and amount of vacuum drawn on an interior of the oven. The vacuum oven will also have some methodology for opening and closing the oven for placing items into and removing items from the oven, either in batches or potentially in an at least somewhat continuous manner, and either being manual or automatic in operation (or some hybrid thereof). Finally, a return port/valve is typically provided through which air/gas can be re-introduced into the interior of the vacuum oven (which return port/valve could merely be associated with an openable door for the oven and/or airflow through the vacuum pump in a reverse direction back into the oven).

The vacuum oven is preferably of a type which includes a window therein, so that items within the oven can be viewed while the vacuum oven is in operation. Typically, a light is also contained within the vacuum oven to enhance visibility of objects therein. As an alternative to a window (or in addition), a camera could be placed within the vacuum oven for viewing of objects within the vacuum oven during operation thereof (and/or to facilitate automatic control). A cold trap container is located upstream of the vacuum pump and downstream from the vacuum oven. The cold trap is configured so that condensable constituents can condense after exiting the vacuum oven. This cold trap/condenser is typically upstream of the vacuum pump, so that the cold trap is between the vacuum oven chamber and the vacuum pump.

The separatory funnel for use with this invention is of a type which has a single input and multiple outputs, at least one of the outputs sized sufficiently small to allow for funneling of liquids into a bottle or other container with a relatively small opening thereinto, or with an outlet which can conveniently direct the fluids into containers as desired. One or more of the discharges from the separatory funnel could be collected as final products of the process, or at least some discharges can be for products that could be disposed of or recycled.

According to the method of this invention, the cannabis crude oil is placed within a liquid supporting container which is then placed into the vacuum oven. The container is preferably of a type which has at least one clear (or at least somewhat transparent) side wall, so that the liquid therein can be viewed from the side. Preferably the container material can withstand thermal shock to some degree without fracture. Preferably the container is significantly larger than the amount of crude oil to be contained therein, such as with a volume at least twice that of the amount of crude oil to be processed into terpene extract.

The cannabis crude oil and container are placed into the vacuum oven, typically through an openable door, and the door is sealed closed. A simplest form of this invention allows the gas within the vacuum oven to merely be ambient air. As an alternative, other gases could be provided within the vacuum oven, through appropriate gas sources, purge valves, etc., as is known in the art. The oven is then caused to heat the crude oil slowly to between 100° F. and 160° F., and in one effective example to about 120° F., typically while standard atmospheric pressure is maintained within the vacuum oven. Preferably such heating occurs over a long period of time, such as approximately two hours, so that all of the crude oil is elevated to this temperature, but none of the crude oil is caused to be significantly hotter, such that excessive evaporation is minimized. Temperature raise taking longer than two hours is less desirable.

After the cannabis crude oil has been elevated to this temperature, the vacuum pump is turned on and a vacuum is pulled on the chamber of the vacuum oven. The cannabis crude oil within the container is watched while this vacuum is pulled on the chamber within the vacuum oven. A surface of the crude oil will begin to climb up within the container, in a manner akin to a liquid boiling into a gas. The vacuum pump is regulated, such as by actuation of a control valve, while an operator watches the surface level of the cannabis crude oil within the container, to make sure that the cannabis crude oil does not "boil over" the top of the container. Rather, the level of the cannabis crude oil is held above its original position but below a top of the container. It is conceivable that an automated control system could use machine vision to follow the rising of the cannabis crude oil within the container and a control system could be provided to control the vacuum within the vacuum oven to keep a level of the cannabis crude oil elevated but below a top of the container. As an alternative to machine vision, an appropriate float sensor or other liquid level sensor could alternatively be utilized in such a control system.

As terpenes are extracted from the cannabis crude oil, it will generally take a larger and larger amount of vacuum to keep the surface of the cannabis crude oil elevated. Finally, controlling of the vacuum pump can stop, allowing the vacuum pump to operate at full capacity until a full vacuum (such as pulling at least 28.6 inches of mercury) has been achieved in the oven. If desired, less than a full vacuum could be pulled on the vacuum oven, such as if it is desired to keep first terpenes extracted from the cannabis crude oil separate from other terpenes and other constituents which might be extracted later.

After the vacuum pump has achieved full operating level, an amount of time is allowed to lapse which is selected by a user, depending on the amount and quality of terpenes to be extracted and depending to some extent on the quality and characteristics of the cannabis crude oil which is provided as the starting material. When a preselected amount of elapsed time has passed, the process of extracting terpenes from the cannabis crude oil is essentially complete, and the remaining step of condensing and collecting the terpenes from the cold trap is initiated. Such condensing and collecting typically first involves turning off the vacuum oven and turning off the vacuum pump, and removing the condensed terpenes from a condensate containing portion of the cold trap/condenser.

The cold trap/condenser preferably maintains a temperature of −50° C. therein in one effective example. To maintain this temperature, heat is removed from the cold trap either through conduction, or convection, or some other heat transfer methodology or combination of cooling technologies. With such a low temperature within the cold trap, the terpenes which were removed from the cannabis crude oil and exited the vacuum oven as a gas, upon encountering these cooler temperatures in the cold trap, and/or also potentially elevated pressures, such as by some form of re-pressurization of the terpene condensate, terpenes are caused to re-condense into a liquid form.

As a liquid, the terpenes collect within an appropriate condensate collection container within the cold trap. This container can then be removed and the terpenes poured through a separatory funnel into a final suitable storage container.

This separatory funnel could merely include a screen for screening out any solids or other debris which might have precipitated within the cold trap. As an alternative, the separatory funnel could separate the terpenes from other constituents condensing within the cold trap as a liquid, such as based on specific gravity of the terpenes versus other liquid constituents, or based on other characteristics such as viscosity, affinity for different items provided in the separatory funnel for separation purposes, or utilizing other separation technology, known in the art for separating liquids.

Finally, the separated terpenes are collected within a suitable storage container, such as a bottle with a closable and sealable cap or lid. The terpenes are then ready for storage, shipping, handling, or other use in other processes.

These terpenes could be further refined and separated if desired, such as through further processing techniques such as fractional distillation, chromatography, centrifugation, or other separation and/or refining techniques. The resulting terpenes are a 100% natural extract of the cannabis plant, especially when initial primary extraction techniques are utilized which are free from the addition of non-naturally occurring substances, and other primary extraction techniques are used which are known to avoid addition of foreign and non-natural substances into the cannabis crude oil. The resulting terpenes are also free of terpenoids or other artificial constituents. The terpenes are then available for use in a variety of different end products, as is known in the prior art, and as will likely be developed in the future, so that the desirable attributes of such terpenes can be imparted upon other items.

OBJECTS OF THE INVENTION

Accordingly, a primary object of the present invention is to provide a method for extracting terpenes from plant-based oils.

Another object of the present invention is to provide a method for terpene extraction especially from oils derived from a cannabis plant.

Another object of the present invention is to provide a method for terpene extraction which is sustainable.

Another object of the present invention is to provide a method for terpene extraction which results in high quality and high purity all natural terpenes being extracted and collected.

Another object of the present mention is to provide a method for terpene extraction which can be practiced with existing equipment and at a low price, and following procedures which are easy to follow.

Another object of the present invention is to provide a system for terpene extraction, especially adapted for use in extracting terpenes from cannabis crude oil.

Other further objects of the present invention will become apparent from a careful reading of the included drawing figures, the claims and detailed description of the invention.

DESCRIPTION OF THE PREFERRED EMBODIMENT

Figure 1:
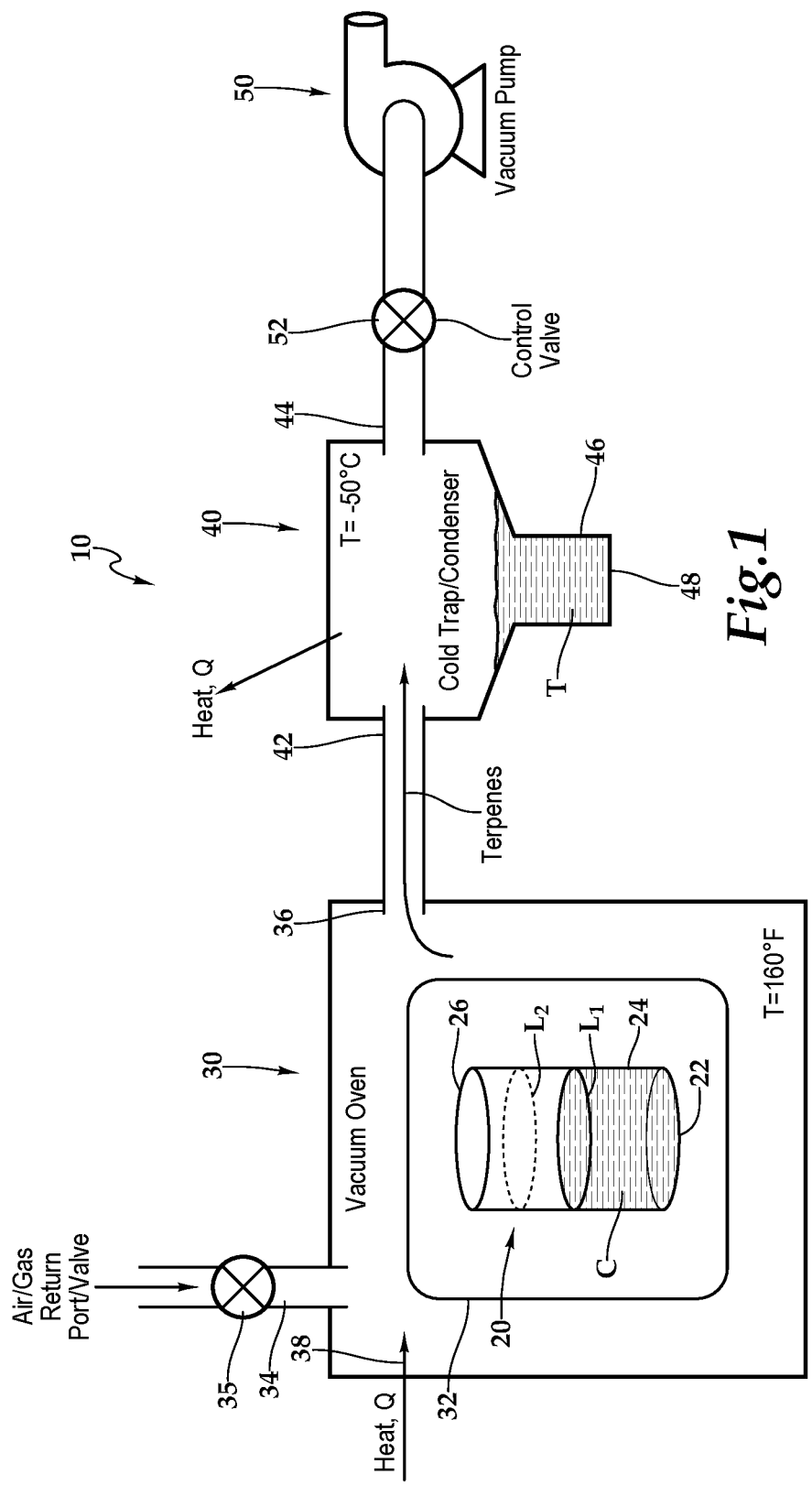
FIG. 1 is a schematic illustrating elements of a system which can implement the method of this invention, the system shown according to one embodiment.

Referring to the drawings, wherein like reference numerals represent like parts throughout the various drawing figures, reference numeral 10 is directed to a system (FIG. 1) which can be used as one configuration to practice the terpene extraction method according to various embodiments of this invention. One such method 100 is also disclosed in FIG. 2.

In essence, and with particular reference to FIG. 1, basic details of the system 10 are disclosed as one embodiment for use in practicing the method of this invention. A raw/crude oil from a plant-based product, such as taken from portions of the cannabis plant, is placed within a container such as the container 20. The container 20 and oil therein are placed within a vacuum oven 30 which is configured to both heat and draw a vacuum on contents within the vacuum oven 30. A cold trap 40 is provided along a gaseous outlet path from the vacuum oven 30. The cold trap 40 is configured to maintain a low temperature therein to cause condensation of vapors extracted from the vacuum oven 30, including terpenes which volatilize from the oil within the container 20 when heated and depressurized within the vacuum oven 30. The cold trap 40 is also in gaseous communication upstream of a vacuum pump 50, which draws the vacuum on both the cold trap 40 and vacuum oven 30. As explained in FIG. 2, particular utilization of this system 10 (or a generally analogous system) according to various methods, including the example method 100 (FIG. 2), provides for a sustainable process 100 for high purity extraction of naturally occurring terpenes from an initial oil, such as crude oil derived from the cannabis plant.

More specifically, and with continuing reference to FIG. 1, specific details of the system 10 are described, which can be used to practice methods such as those disclosed herein for terpene extraction. A first element of the system 10 is a container 20 which contains the crude oil from which the terpenes are to be extracted. This container could be any of a variety of open top containers. It is also conceivable that the container could have some more complex upper portion but still generally be of a variety which allows for volatilization of vapors from a liquid placed within the container from upper portions of the oil within the container, and still be considered to be an "open top" container, even if some form of hood or cover is also associated with the container.

The container 20, in a simplest embodiment is merely cylindrical in shape with a circular floor 22 and cylindrical side walls 24 extending up from the circular floor 22 to a rim 26. In other embodiments, the container 20 could have a cross-section (taken horizontally) that is other than circular, including square, oval, and other cross-sectional shapes. One container 20, according to this invention, has a somewhat elongated form with a height between the floor 26 and the rim 22 greater than a width defined by a diameter of the floor 22, such as with the container 20 in embodiment disclosed. Such an aspect ratio, in one embodiment is between one and two.

In other embodiments, the container 20 could be more shallow, and having an aspect ratio of less than one, so that the diameter or other width of the container 20 is greater than a height of the container 20. At the other extreme, the container 20 could have a more deep configuration with an aspect ratio higher than two, and with the height more than double the width of the container 20. With different aspect ratios, a ratio of surface area of the oil C contained within the container 20 to the volume of this oil C, is modified. This can cause different rates of volatilization of vapors out of the oil C, so that shape of the container 20 can be optimized along with other elements of the system 10, according to different embodiments of the method and process 100 of various embodiments of this invention, to produce optimal terpene extraction from oil contained with in the container 20.

The container 20 preferably has at least partially transparent sidewalls 24, so that a level of oil C within the container 20 can be viewed, such as through a window 32 in the oven 30, during heating and drawing of a vacuum within the oven 30. In particular, during initial drawing of a vacuum on the oil C with in the container 20, an original level $L_1$ (also called a "starting elevation") of the oil C within the container 20 will change to an elevated froth level $L_2$ (also called a "froth level") for the oil C within the container 20. It is desirable to keep the oil C from boiling over, so that sidewalls 24 of the container 20, being transparent, assists an operator (or machine vision control system) to best be able to view the level of the oil C within the container 20 during operation of the method of this invention, according to various embodiments.

Figure 2:
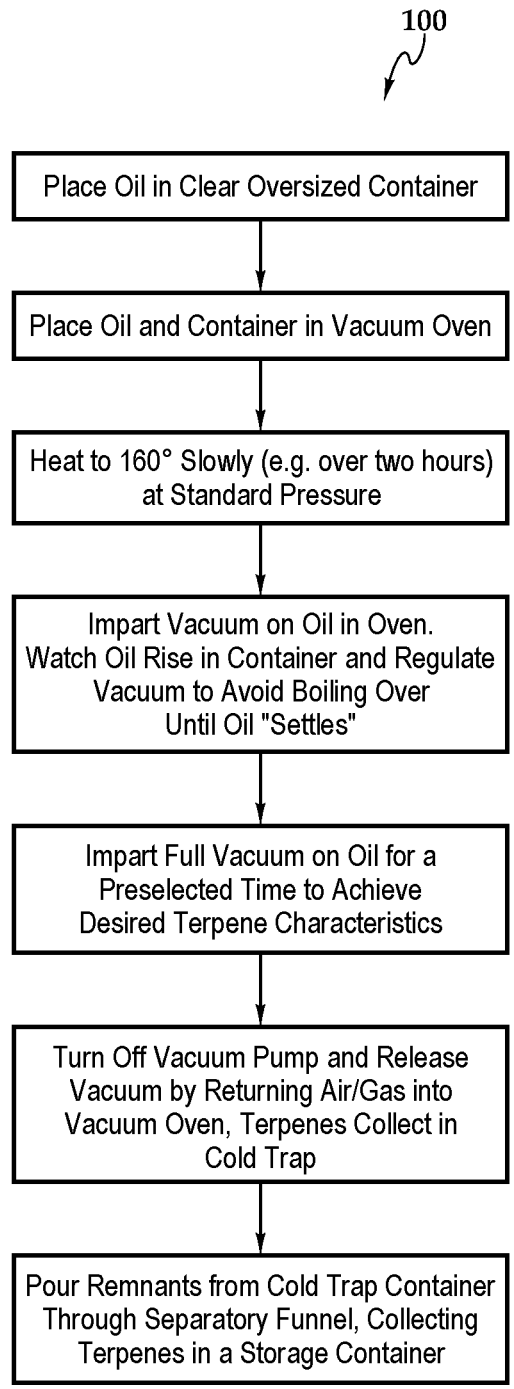
FIG. 2 is a flow chart including steps in the method of this invention according to one embodiment, for extracting terpenes from an oil or other liquid produced from plant-based material, such as portions of the cannabis plant.

The container 20 is preferably oversized relative to a volume of oil C to be processed. Stated alternatively, the container 20 is preferably only filled partway with oil C. In one embodiment, the container 20 has a volume which is at least about double a volume of oil C to be processed within one cycle of the method 100 implemented by the system 10 of this invention (FIG. 2). In one embodiment, horizontal lines can be placed upon a container 20 as a guide to operators, such as with a lower line defining a fill line for oil C initially placed with in the container 20, and a second horizontal line defining a recommended maximum elevation line for contents of the container 20 when a vacuum is pulled on the interior of the vacuum oven 30, causing the oil C to have an elevated surface during certain portions of the method of this invention.

While the container 20 is shown with vertical sidewalls 24, it is conceivable that the container 20 could have tapering sidewalls, which typically (if tapering) would taper to a greater width/diameter as the container 20 portions extend upward from the floor 22, so that the container 20 would have a larger width/diameter at the rim 26 than at the floor 22. With such a geometry, less fine control of the rate at which a vacuum is drawn on an interior of the vacuum oven 30 could still keep the oil C from boiling over the rim 26 of the container 20, because as boiling and volatilization and froth on a surface of the oil C is initiated by drawing a vacuum on the oil C, the diameter of the surface of the oil C would become progressively greater, due to the tapering of the sidewalls 24, and act to decrease a rate at which the surface of the oil C would climb within the container 20.

The oil C within the container 20 is, according to various embodiment of this invention, in the form of cannabis crude oil C. This cannabis crude oil C is initially provided by a primary extraction process. Such a primary extraction involves producing the cannabis crude oil from various solid portions of the cannabis plant, according to primary extraction techniques known in the prior art. These primary extraction techniques can include extraction by heat and/or pressure, ethanol extraction, hydrocarbon extraction, steam extraction, carbon dioxide extraction, etc. This invention is not directed to the particular method of primary extraction involved. Rather, the method 100 of this invention begins with the cannabis crude oil C which was produced from some formerly primary extraction process.

With continuing reference to FIG. 1, details of the vacuum oven 30 are described, which can hold the container 20 of oil C during implementation of the method 100 according to various embodiments of this invention. The vacuum oven 30 is generally an enclosure into which heat can be added, such as from heat source 38. The oven 30 is also sealed so that an atmosphere within the vacuum oven 30 can be controlled, at least as to pressure therein. The oven 30 in one embodiment is a generally orthorhombic enclosure which, in one embodiment, has a similar height to its width and depth, so that it is approximately cubic in shape. Other orthorhombic shapes could alternatively be provided for the vacuum oven. The vacuum oven 30 is typically provided to hold a single container 20 during implementation of the method 100 of this invention. However, the oven 30 could be oversized and simultaneously process multiple containers 20 of oil C.

Typically, the vacuum oven 30 is of a type where the heat source 38 does not alter the environment within an interior of the vacuum oven 30, such as with an open flame. Electric heat from heating elements would be one suitable form of heat source 38 for the vacuum oven 30. Other sources of heat could alternatively be provided including microwave energy heat sources, various different conduction, convection or radiation heat sources, etc. The heat source 30 is preferably controllable, such as with a thermostatic control, so that a temperature of an atmosphere within the vacuum oven 30 can be carefully controlled.

Beneficially, the vacuum oven 30 includes a window 32 so that the container 20 and oil C within the vacuum oven 30 can be viewed. A light can also be provided within the oven 30, and some form of shelf or other platform, upon which the container 20 can be placed. As an alternative to the window 32, a camera could be placed in the oven 30 and a monitor coupled to the camera, so that the container 20 and oil C can be viewed in a manner other than through the window 32.

The oven 30 includes an inlet 34 for gases to pass thereinto, which preferably includes a valve 35 thereon which can be opened or closed. An outlet 36 extends away from the oven 30, and with this system 10, leads to the cold trap 40 downstream of the vacuum oven 30. The inlet 34 provides a pathway for gases, such as air, to be initially placed into the vacuum oven 30, and for restoration of atmospheric pressure, such as after completion of the method 100 of this invention, and when it is desired to open a door of the vacuum oven 30, such as to remove the container 20 after completion of the method 100.

This door into the oven 30 is preferably sealed, along with other portions of the enclosure of the oven 30, so that different pressure levels within the vacuum oven 30 can be maintained. Typically, pressure sensors are provided within the vacuum oven 30, so that operators can monitor pressure within the vacuum oven 30. Such a pressure sensor can be included within a control system which also includes the vacuum pump 50 and a control valve 52 upstream of the vacuum pump 50, so the pressure within the vacuum oven 30 can be carefully controlled between generally atmospheric pressures pressure levels below atmospheric pressure.

While primary embodiments disclose only involve handling of the oil C at atmospheric pressure or below atmospheric pressure, it is conceivable, especially during early steps in the method of this invention, that such steps could occur at an elevated pressure above atmospheric pressure. In such alternative embodiments, elevated pressure within the vacuum oven 20 could be achieved by including a compressor/pump along the inlet 34 pathway leading into the vacuum oven 30.

The vacuum oven 30 preferably includes timer accessories associated therewith. Such timer accessories preferably are a type which can have a certain amount of time programmed thereinto, and then to have some form of buzzer or other signal provided after a preset amount of time has elapsed. In other embodiments, the timer could be integrated into a control system so that when certain amounts of time have elapsed, other processes would automatically be initiated. Starting of the timer could be manual starting, or starting of the timer could begin when a pre-programmed threshold temperature has been obtained within the vacuum oven 30.

The heat source 38 is preferably configured so that it can raise the temperature within the vacuum oven at different rates, so that a most preferred slow rate of heating can be selected and utilized according to this invention. In one embodiment, the oven 30 is raising the temperature approximately 40° F. (from about a standard atmospheric temperature of 60° F. to about 120° F.) over a one to two hour period, so that a rate of heating is only 20° F. to 40° F. per hour (e.g. less than 1° F. of heating per minute).

With continuing reference to FIG. 1, details of the cold trap 40 are described, according to one embodiment of the system 10 of this invention. With some vacuum ovens 30, cold traps 40 are integrated thereinto or can be added to the oven 30 as an accessory, so that these elements (the vacuum oven 30 and the cold trap 40) are integrated together to some extent. Such integration can include sharing walls thereof, sharing control systems, sharing power sources, etc. In other embodiments, the cold trap 40 is a separate element downstream of the oven 30 without integration between the cold trap 40 and the vacuum oven 30, other than the provision of a conduit extending from the outlet 36 of the oven 30 to an entrance 42 into the cold trap 40.

The cold trap 40 is a walled enclosure, typically which is insulated at walls thereof, to minimize rates of heat transfer into and out of the cold trap 40 from a surrounding environment. The entrance 42 leads into the cold trap 40. A gas exit 44 leads away from the cold trap 40 and leads to the vacuum pump 50 and an associated control valve 52 between the cold trap 40 and vacuum pump 50, for control of the system 10 of this invention according to various different embodiments. The cold trap 40 also includes a collection sump 46 at a lower portion of the cold trap 40. This collection sump 46 also preferably includes some form of liquid exit 48, such as a pipe with a stopcock or other control valve thereon, to control flow of condensed liquids out of the collection sump 46 of the cold trap 40, into other containers.

The cold trap 40 includes a heat transfer subsystem configured to remove heat from the cold trap 40, so the temperature within the cold trap 40 can be maintained below ambient temperature conditions. In one embodiment, this heat transfer subsystem is able to reduce a temperature within the cold trap 40°–50° C. At a minimum, the cold trap 40 maintains temperatures below ambient temperatures, such as about 20° C., and more typically below 0° C., and most preferably even colder, such as −50° C.

In one embodiment, this heat transfer subsystem is in the form of a refrigeration system with refrigerant elements, such as in the form of tubes carrying a refrigerant working fluid therein, transporting the cold refrigerant within such pipes, and with such pipes having walls thereof exposed within an interior of the cold trap 40. With such an arrangement, as gases, and especially terpene containing vapors pass from the vacuum oven 30, through the outlet 36 of the oven 30 to the entrance 42 at the cold trap 40, these vapors will pass close to or into contact with the tubes of this cooling subsystem, and cause these vapors to be significantly reduced in temperature.

Terpene vapors have a condensation point above the temperature maintained within the cold trap 40, so that the terpene vapors condense into a liquid. Typically, this condensation would occur to a greatest extent upon surfaces of the cooling subsystem, which carry the refrigerant therein. These terpene T condensate liquids would then collect to a sufficiently great extent that they would fall as droplets down from the tubes (or other heat transfer surface maintained at a low temperature) and collect within the sump 46 at a lower portion of the cold trap 40.

In one embodiment, an upper portion of the cold trap 40 is larger than the collection sump 46, and with a funneling and tapering transition between upper portions of the cold trap 40, and lower portions of the cold trap 40, defined by the collection sump 46. Such a tapering wall assists in concentrating the condensing terpene vapors within the collection sump 46. By making upper portions of the cold trap 40 larger in volume than the collection sump 46, and by placing portions of the heat transfer subsystem, such as including refrigerant liquid carrying tubes within this upper portion of the cold trap 40, a large area is provided for terpene vapors to come into contact with surfaces of such pipes, for efficient heat transfer to the terpene vapors, and condensation thereof.

Most preferably, the entrance 46 of the cold trap 40 and gas exit 44 of the cold trap 40 are provided on opposite lateral sides of the cold trap 40, to minimize the potential for terpene vapors to pass through the cold trap 40 without condensation. Baffles or other gaseous flow pathway lengthening structures can be provided to provide a long path for gases through the cold trap 40, to further minimize any potential for terpene vapors to find their way entirely through the cold trap 40 without condensation therein. Rather, substantially only non-terpene gases originally within the vacuum oven 30 would pass out of the gas exit 44 of the cold trap 40, such as air originally within the vacuum oven 30. Preferably dry air is initially placed within the vacuum oven 30, so that condensation of water vapor with in the cold trap 40 can be minimized or eliminated, and so that liquids condensed with in the cold trap 40 are high purity terpene T liquid.

Once the terpenes T have collected within the sump 46, (or during such collection) the liquid exit 48 can be opened for pouring of the terpenes T into other collection containers. Typically, a separatory funnel is provided below the liquid exit 48 for further separation of the terpenes T into different terpene T constituents, for separate collection and use. The separatory funnel could operate on various different separation principles known in the prior art, which separation methodologies could be based upon one or more of separation based on differential specific gravity, viscosity, affinity or repulsion relative to different items provided within the separatory funnel for separation purposes, or utilizing other separation technologies known in the liquid separating arts.

The gas exit 44 of the cold trap 40 leads to a control valve 52 upstream of a vacuum pump 50. As described above, this vacuum pump 50 is preferably controlled in conjunction with the vacuum oven 30, but with the control valve 52 preferably being manually controllable by an operator while the operator is viewing the oil C within the container 20 inside of the oven 30. In one embodiment, this control valve 52 is a manually graspable lever which has relatively fine control for an operator so that precise control of vacuum drawn on the vacuum oven 30 can occur, and boiling over of the oil C within the container 20 can be avoided. As an alternative, the control valve 52 could be automated, such as by being controlled by a control system which includes some form of oil C level sensors within the container 20, so that automatic control is provided to prevent boiling over and optimization of the terpene extraction process according to various embodiments of this invention.

With particular reference to FIG. 2, details of the method 100 of this invention are described, according to one embodiment of terpene T extraction. Initially the oil C is placed into the container 20. This container 20 is then placed within the vacuum oven 30. If desired, some form of customized atmosphere can also be provided within the vacuum oven 30, such as dry air, or a pure and relatively non-reactive gas such as nitrogen or argon. If desired, the vacuum oven 30 could be pressurized somewhat above atmospheric pressure, or could maintain the atmosphere therein at standard atmospheric pressure.

Heat is then slowly applied to raise the temperature of the atmosphere and to raise the temperature of the oil C within the oven 30. In particular, the heating occurs to no more than 160° F. (and only 120° F. in some instances) occurs over a relatively long period of time, such as approximately one to two hours of time. During this step, it is believed that raising the temperature too quickly will cause premature volatilization of some of the terpenes within the oil C, rather than a more beneficial rapid extraction process assisted by vacuum after the oil C has reached a uniform elevated temperature, such as 120° F. Furthermore, such slow heating is beneficial in that the oil C is kept from having any portions thereof elevated in temperature significantly above the target temperature (or some other maximum, such as 160° F.), which can cause decay of desirable terpene molecules, and/or loss of such molecules through premature volatilization. In one embodiment, the oven 30 is first heated at any speed to the target temperature, such as 160° E Then the crude oil C is placed in to the oven 30. The size of the container 20 and the amount of oil C can be selected so that the rate of heating is slow enough to produce the desired results. Time is still allowed for the heating to occur before the next step.

After the oil C has fully reached this target temperature (and in one embodiment, the oven is turned down, such as from 160° F. to 140° F.), the vacuum is imparted on the interior of the oven 30, such as by activation of the vacuum pump 50. This causes a surface of the oil C within the container 20 to be elevated, from original level $L_1$ to an elevated level $L_2$. Without intervention, this froth level $L_2$ would typically pass over the rim 26 and spill out of the container 20. To keep this from happening, the control valve 50 is throttled to a rate at which vacuum pump 50 only draws a vacuum on the oven 30 at a limited rate, controlled through control valve 52 adjustment, and so that no boiling over occurs. During this initial phase of drawing a vacuum on the oven 30, some terpenes T volatilize, pass out of the oven 30 along the outlet 36, and into the cold trap 40 through the entrance 42, where they condense and collect within the sump 46.

After an initial period where active control of the elevated level $L_2$ of the oil C within the container 20 is required, the elevated level $L_2$ of the oil C within the container 20 tends to settle back down to near the original level $L_1$. After such settling has occurred, the control valve 52 can be fully opened and full vacuum drawn on the vacuum oven 30, without significant further froth or other elevation of the surface of the oil C within the container 20. The full vacuum draw level, in one embodiment pulls the pressure in the oven 30 down to 28.6 inHg. Other pressures could be targeted in other embodiments. A preselected amount of time is allowed to elapse while terpenes continue to volatilize out of the oil C.

This preselected amount of time can be selected based on the particular terpene constituents desired to be extracted from the oil C at the end of this process. For instance, and speaking generally, terpenes having a larger molecular weight will tend to be the last terpenes T to volatilize and leave the oil C and pass on to the cold trap 40 for condensation and collection within the sump 46. If a larger amount of such high molecular weight terpenes T are desired to be extracted, the pre-selected time would be longer, so that a greater amount of such larger molecular weight terpenes T could be collected. Alternatively, if it is desirable to minimize such larger molecular weight terpenes T within the final terpenes T extracted and collected, this predetermined amount of time would be shorter. Through repeated experiments, an operator can determine optimal concentrations of different terpenes T in the final condensed liquid terpenes T to be removed and extracted according to this invention, and an appropriate time to achieve that result would be then followed in future extraction processes to provide an identical (or near identical) extracted terpene T formulation.

Once the predetermined amount of time has passed, the vacuum pump 50 is turned off, and air/gas is allowed to return into the oven 30, either through the inlet 34, by opening the valve 35, or by merely allowing air to flow in reverse direction through the vacuum pump 50, through the control valve 52, through the cold trap 40, and back into the vacuum oven 30.

Finally, the extracted terpenes T within the collection sump 46 can be passed through the separatory funnel to separate terpenes T having different characteristics from each other and for final separate collection and appropriate use. Remaining portions of the oil C within the oven 30 could be merely disposed of, or could be utilized according to some other beneficial use to which the remaining oil C, depleted of a large measure of terpenes T, might beneficially be utilized. The system 10 is then ready for reuse with a new batch of oil C, and the process repeated.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified.

What is claimed is:

1. A method for extraction of terpenes from a cannabis plant, including the steps of:
    obtaining cannabis crude oil which originated from a cannabis plant;
    placing the cannabis crude oil into a vacuum oven while contained within a container having a volume greater than an amount of cannabis crude oil contained therein;
    raising a temperature of the cannabis crude oil to an elevated temperature above a standard atmospheric temperature of 60° F.;
    drawing a vacuum on the cannabis crude oil within the vacuum oven at the elevated temperature;
    regulating an amount of vacuum drawn on the vacuum oven to keep a surface level of the cannabis crude oil elevated above a starting elevation which existed before the vacuum was drawn on the vacuum oven, and below a top of the container;
    orienting a cold trap downstream from the vacuum oven and upstream from a vacuum pump, the cold trap maintaining a temperature sufficiently low that terpenes volatilized from the cannabis crude oil within the vacuum oven are caused to condense within the cold trap; and
    collecting terpene liquids from the cold trap into a terpene product container.

2. The method of claim 1 wherein the vacuum oven includes a window and the container has an at least partially transparent side wall.

3. The method of claim 1 wherein said regulating step is followed by a step of operating the vacuum pump at full power.

4. The method of claim 3 wherein said vacuum pump is operated at full power for a predetermined amount of time selected by an operator.

5. The method of claim 1 wherein said raising a temperature step occurs for a time period of at least about one hour.

6. The method of claim 5 wherein said raising a temperature step occurs for a time period of less than about two hours.

7. The method of claim 1 wherein said raising a temperature step raises the temperature up to 100° F.

8. The method of claim 7 wherein said raising a temperature step raises the temperature up to no greater than 160° F.

9. The method of claim 8 wherein said raising a temperature step raises the temperature up to about 120° F.

10. The method of claim 1 wherein said placing step includes said container filled less than about half full with cannabis crude oil.

11. The method of claim 1 wherein said regulating step includes throttling a valve adjacent to a source of the vacuum of said drawing step, such that a rate of evacuation of gases from the vacuum oven is regulated.

12. A method for terpene extraction, including the steps of:
    placing an oil containing terpenes into a vacuum oven while the oil is located within a container;
    raising a temperature of the oil to an elevated temperature above a standard atmospheric temperature of 60° F.;
    drawing a vacuum on the oil within the vacuum oven at the elevated temperature; and
    condensing terpene gases pulled from the oil by the vacuum in a cold trap between the vacuum oven and a vacuum pump, the cold trap colder than the vacuum oven.

13. The method of claim 12 including the further step of regulating an amount of vacuum drawn on the vacuum oven to keep a surface of the oil elevated above a starting elevation which existed before the vacuum was drawn on the vacuum oven, and below a top of the container.

14. The method of claim 13 including the further step of manually viewing oil within the container within the vacuum oven, and throttling the vacuum to control an elevation of the oil within the container.

15. The method of claim 14 wherein said viewing step includes viewing through a window in the vacuum oven.

16. The method of claim 15 wherein said regulating step includes the container being oversized to be at least double a volume of oil initially placed within the container.

17. The method of claim 13 wherein said regulating step includes automatically regulating a level of the surface of the oil, with a vacuum pump having a control valve coupled to a control system which automatically adjusts vacuum within the vacuum oven responsive to sensing of a level of the oil within the container.

18. The method of claim 12 wherein said condensing step includes the cold trap having a temperature below 0° C.

19. The method of claim 18 wherein said condensing step includes the cold trap including a sump at a lower portion of the cold trap for condensing of terpenes therein.

20. The method of claim 18 including the further step of separating terpenes from said condensing step utilizing a separatory funnel into different constituents of the terpenes.

* * * * *